US010120543B2

United States Patent
Sugumaran et al.

(10) Patent No.: US 10,120,543 B2
(45) Date of Patent: Nov. 6, 2018

(54) PLANT EMERGENCE SYSTEM

(71) Applicant: Deere & Company, Moline, IL (US)

(72) Inventors: Ramanathan Sugumaran, Bettendorf, IA (US); Marc Lemoine, Bettendorf, IA (US); Federico Pardina-Malbran, Fort Collins, CO (US)

(73) Assignee: Deere & Company, Moline, IL (US)

( * ) Notice: Subject to any disclaimer, the term of this patent is extended or adjusted under 35 U.S.C. 154(b) by 291 days.

(21) Appl. No.: 15/018,994

(22) Filed: Feb. 9, 2016

(65) Prior Publication Data

US 2017/0228118 A1 Aug. 10, 2017

(51) Int. Cl.
| | |
|---|---|
| *G06K 9/00* | (2006.01) |
| *G06F 3/0484* | (2013.01) |
| *G06F 17/30* | (2006.01) |
| *G06F 3/0482* | (2013.01) |
| *G01N 33/00* | (2006.01) |
| *G06T 7/00* | (2017.01) |

(52) U.S. Cl.
CPC ....... *G06F 3/0484* (2013.01); *G01N 33/0098* (2013.01); *G06F 3/0482* (2013.01); *G06F 17/30241* (2013.01); *G06F 17/30268* (2013.01); *G06T 7/0004* (2013.01); *G06T 2207/10024* (2013.01); *G06T 2207/10036* (2013.01); *G06T 2207/20021* (2013.01); *G06T 2207/30188* (2013.01)

(58) Field of Classification Search
CPC ......... G06F 17/30241; G06F 17/30268; G06F 3/0482; G06F 3/0484; G01N 33/0098; G01N 21/29; G01N 2201/12; G06T 7/00; G06T 2207/30188
See application file for complete search history.

(56) References Cited

U.S. PATENT DOCUMENTS

| | | | | |
|---|---|---|---|---|
| 2008/0052538 A1* | 2/2008 | Scheidt | ..................... | H04L 9/00 713/193 |
| 2008/0065287 A1* | 3/2008 | Han | ..................... | A01B 69/007 701/28 |
| 2011/0231484 A1* | 9/2011 | Burgess, III | .......... | G06F 3/0346 709/203 |
| 2014/0230580 A1* | 8/2014 | Dybro | .................. | A01D 45/021 73/865 |

(Continued)

FOREIGN PATENT DOCUMENTS

WO 2013059399 A1 4/2013

OTHER PUBLICATIONS

Weyrich et al (Quality assessment of row crop plants by using a machine vision system, 2013, IEEE).*

*Primary Examiner* — Amara Abdi
(74) *Attorney, Agent, or Firm* — Joseph R. Kelly; Kelly, Holt & Christenson, PLLC

(57) ABSTRACT

An unmanned image capture system captures images of a field or work area using a first, spectral image capture system and a second video image capture system. Crop location data that is indicative of the location of crop plants within the field, is obtained. Evaluation zones in the image data generated by the first image capture system are identified based on the crop location data. Crop plants within the evaluation zones are then identified, analyzed to generate a corresponding emergence metric, and linked to a corresponding video image generated by the second image capture system.

18 Claims, 16 Drawing Sheets

(56) References Cited

U.S. PATENT DOCUMENTS

| | | | |
|---|---|---|---|
| 2014/0285672 A1* | 9/2014 | Hogasten | H04N 5/33 348/164 |
| 2014/0285673 A1* | 9/2014 | Hundley | G06K 9/00657 348/164 |
| 2015/0278640 A1* | 10/2015 | Johnson | G06K 9/00657 382/110 |
| 2017/0031577 A1* | 2/2017 | Winther Jespersen | G06F 3/04847 |
| 2017/0084039 A1* | 3/2017 | Ritter | G06T 7/194 |

* cited by examiner

FIG. 5B

PLANT EMERGENCE SYSTEM

FIELD OF THE DESCRIPTION

The present description relates to plant emergence. More specifically, the present description relates to plant emergence analysis using images collected from an unmanned system.

BACKGROUND

There are a wide variety of different types of farming techniques. One such technique is referred to as precision farming. Precision farming, or precision agriculture, is also referred to as site-specific crop management. The technique uses observation and measurement of variations of different criteria at specific sites, from field-to-field, and even within a single field. The observation and measurement of the variation in the different criteria can then be acted on in different ways.

The effectiveness of precision farming depends, at least in part, upon the timely gathering of information at a site-specific level, so that information can be used to make better decisions in treating and managing the crop. This type of information can include information that is indicative of plant emergence characteristics (such as maturity, emergence uniformity, etc.) pest presence, disease, water and nutrient levels, weed stresses, etc.

The discussion above is merely provided for general background information and is not intended to be used as an aid in determining the scope of the claimed subject matter.

SUMMARY

An unmanned image capture system captures images of a field or work area using a first spectral image capture system, and a second video image capture system. Crop location data that is indicative of the location of crop plants within the field, is obtained from the planting machines or other historical sources. Evaluation zones in the image data generated by the first image capture system are identified based on the crop location data. Crop plants within the evaluation zones are then identified, analyzed to generate a corresponding plant emergence metric, and linked to a corresponding video image generated by the second image capture system.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIGS. 5A-5C show examples of user interface displays that can be generated by the plant evaluation system.

DETAILED DESCRIPTION

Figure 1:
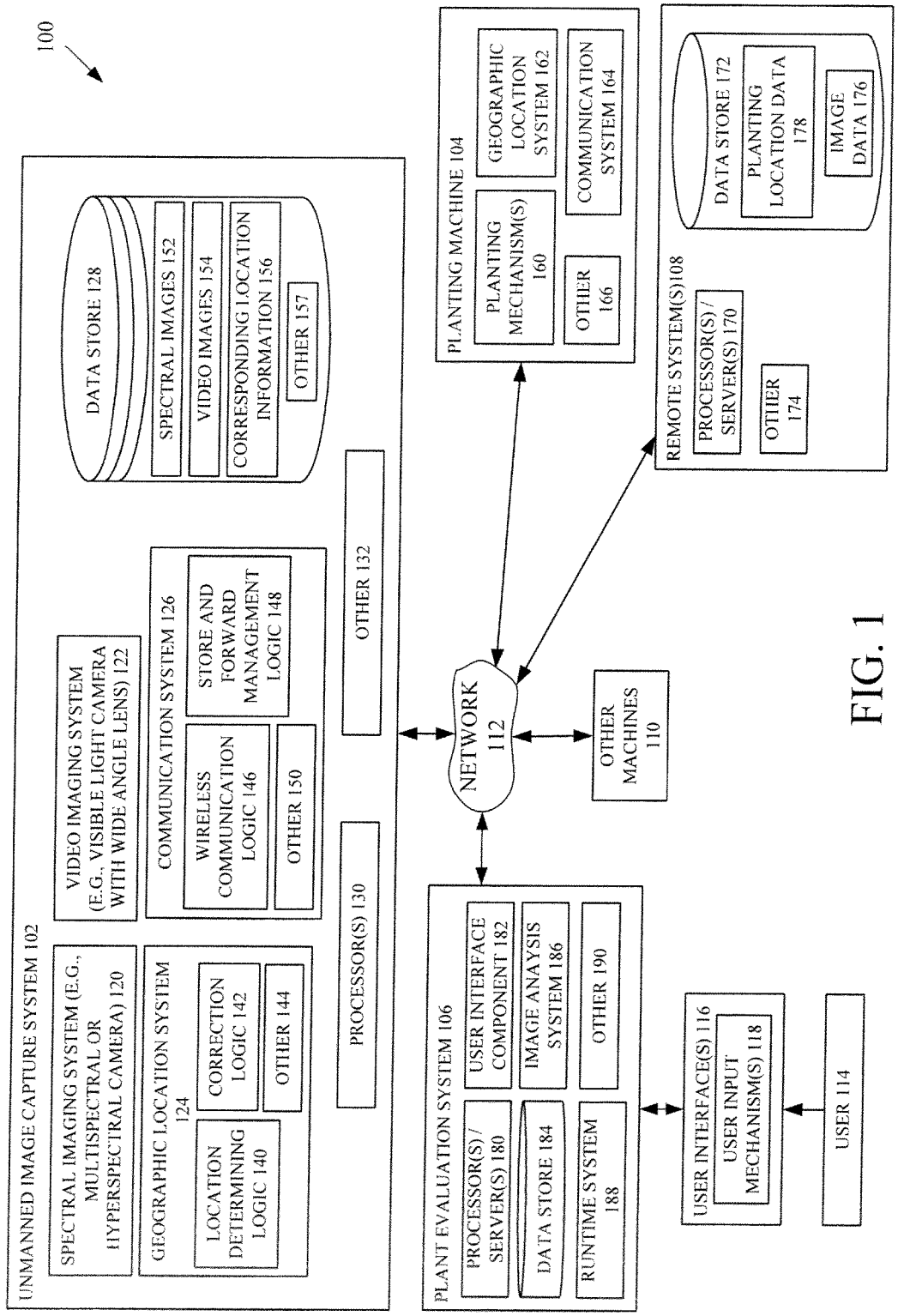
FIG. 1 is a block diagram of one example of a plant analysis architecture.

FIG. 1 is a block diagram of one example of a plant analysis architecture 100. In the example shown in FIG. 1, architecture 100 illustratively includes unmanned image capture system 102, planting machine 104, plant evaluation system 106, and it can include remote systems 108 and other machines 110. Plant evaluation system 106 is shown generating user interfaces 116 with user input mechanisms 118, for access by user 114. User 114 can illustratively interact with user input mechanisms 116 in order to control and manipulate plant evaluation system 106.

Also, in the example shown in FIG. 1, the items are illustratively connected to one another over a network 112. Network 112 can be any of a wide variety of different types of networks, such as the Internet or another wide area network, a variety of other wireless or wired networks, etc.

Before describing the items in architecture 100 in more detail, a brief overview of the operation of architecture 100 will first be provided. In one example, unmanned image capture system 102 includes an unmanned aerial vehicle, although other unmanned systems could be used as well. System 102 illustratively captures spectral images of a field under analysis, as well as video images. Geographic location information is associated with those images, and they are provided to plant evaluation system 106. Planting machine 104, when it planted the crops in the field under analysis, illustratively generated geographic location information that identifies the location of the plants in the field, or the rows of crops in the field using, for instance, RTK GPS system. This information is also provided to plant evaluation system 106. Plant evaluation system 106, itself, illustratively identifies evaluation zones in the field under analysis based on the location of the crops in that field. It then analyzes the spectral images received from image capture system 102 to identify crop plants in the evaluation zones. It evaluates the images of those crop plants to determine an emergence characteristic corresponding to those plants. For instance, it may determine whether the plants are emerging uniformly, ahead of schedule, behind schedule, or not emerging, among other things. It divides the images of the field into grid sections and assigns an emergence summary metric, which is indicative of the emergence characteristics of plants in that grid, to each grid section. It then links the video images of each grid section, also received from image capture system 102, to the grid sections. Then, when a user 114 accesses plant evaluation system 106, the user can illustratively view an image of the grid sections that shows the various emergence summary metrics. Also, the user can easily navigate to the video image so the user can also see a video image of any particular grid section.

A more detailed description of each of the items in architecture 100 will now be provided. System 102 illustratively includes spectral imaging system 120, video imaging system 122, geographic location system 124, communication system 126, data store 128, processor 130, and it can include a wide variety of other items 132, as well. Spectral imaging system 120 illustratively includes a camera that takes spectral images of the field under analysis. For instance, the camera can be a multispectral camera or a hyperspectral camera, or a wide variety of other devices for capturing spectral images. Video imaging system 122 illustratively includes a camera that captures images in the visible or thermal infrared range. For example, it can be a visible light video camera with a wide angle lens, or a wide variety of other video imaging systems.

Geographic location system 124 can include location determining logic 140, correction logic 142, and it can include other items 144. The location determining logic 140 can, for instance, be a satellite navigation receiver that receives satellite information from a positioning satellite. Correction logic 142 can include a correction receiver or transceiver which can, for example, receive correction information from a differential correction base station, or from a satellite, or a real time kinematic information that is used to correct or enhance the precision of, position data received from a global navigation satellite system. In one example, the geographic location information generated by system 124 can have a spatial resolution on the order of several centimeters, once corrected, although less precise systems can just as easily be used. These are examples only, and some other examples of geographic location systems are discussed below.

Communication system 126 illustratively includes wireless communication logic 146, store and forward management logic 148, and it can include other items 150. Wireless communication logic 146 can be substantially any wireless communication system that can be used by image capture system 102 to communicate information to the other items in architecture 100. Store and forward management logic 148 illustratively stores information, when transmission is not possible for whatever reason, and then forwards it once transmission becomes possible again. Some examples of store and forward scenarios are described in further detail below.

Data store 128 illustratively stores the spectral images 152 generated by spectral imaging system 120. It also illustratively stores the video images 154 generated by video imaging system 122. As briefly mentioned above, when the images are taken by imaging systems 120 and 122, geographic location system 124 illustratively generates geographic location information corresponding to a geographic location reflected in those images. Thus, data store 128 illustratively stores the corresponding geographic location information 156 for the spectral images 152 and video images 154 and it can store other items 157 as well.

Planting machine 104 illustratively includes a set of planting mechanisms 160, a geographic location system 162, a communication system 164, and it can include a wide variety of other planting machine functionality 166. As planting machine 104 travels over the field, it plants crop, illustratively in rows, using planting mechanisms 160. Geographic location system 162 can be the same type as geographic location system 124 described above with respect to image capture system 102, or a different type of system. It illustratively generates geographic location information that identifies the geographic location of the crop plants (or at least the rows of crop plants) when they are planted in the field. Communication system 164 can be the same type of system as system 126, or a different type of system. It illustratively communicates the geographic location information identifying the location of the crop plants, or rows, over network 112.

Other machines 110 can include a wide variety of different machines. For example, they can include other planting machines or even other machines that travel over the field to apply pesticides, herbicides, fertilizer, etc.

Remote systems 108 can also be a wide variety of different systems. They can be remote server environments, remote computer systems that may be used, for instance, by a farmer, a farm manager, etc. They can also be remote computing systems, such as mobile devices, remote networks, or a wide variety of other remote systems. In one example, the remote systems 108 include one or more processors or servers 170, data store 172, and they can include other items 174. The remote systems 108 can be configured as a remote server environment that stores the image data 176 generated by image capture system 102 (which can include the spectral images 152, video images 154, and corresponding location information 156) as well as planting location data 178, that is generated by planting machine 104, which indicates the location of crop plants or plant rows in the field. This is just one example of a remote system 108, and a wide variety of others can be used as well.

Plant evaluation system 106 illustratively includes one or more processors or servers 180, a user interface component 182, data store 184, image analysis system 186, runtime system 188, communication component 189, and it can include a wide variety of other items 190. In one example, plant evaluation system 106 can run one or more applications that comprise image analysis system 186 and runtime system 188. Systems 186 and 188 can be embodied as other items as well. Image analysis system 186 illustratively receives the image data (either directly from image capture system 102, or from remote system 108, or from another location), along with the plant location data 178 (either from planting machine 104, remote system 108, or another system). It then evaluates the image data to determine any of a number of different crop characteristics. For instance, it can determine whether the crop is emerging uniformly, at a rate that is ahead of schedule, behind schedule, or that it is not emerging, etc. This analysis is performed by first identifying evaluation zones based upon the location of the crop plants (or rows) in the field, and then performing spectral analysis within those evaluation zones to identify the crops, and various characteristics of those crops.

Runtime system 188 can be used by user 114 to access that information. For instance, the user can control runtime system 188 to display the various images, emergence summary metrics, or other analysis results generated by image analysis system 186. In addition, the user can view video images taken by video imaging system 122 to visually verify, or otherwise evaluate, the veracity of the analysis results. In addition, user 114 can evaluate how to treat the field (or various sites within the field) based upon the analysis results. In one example, image analysis system 186 also generates recommendations for treating various spots within the field, based upon the analysis data. This can vary widely from things such as applying more fertilizer, applying no fertilizer, replanting, etc. Communication component 189 can be used to communicate the analysis results, or other information generated by plant evaluation system 106, to other items in architecture 100 as well.

Figure 2:
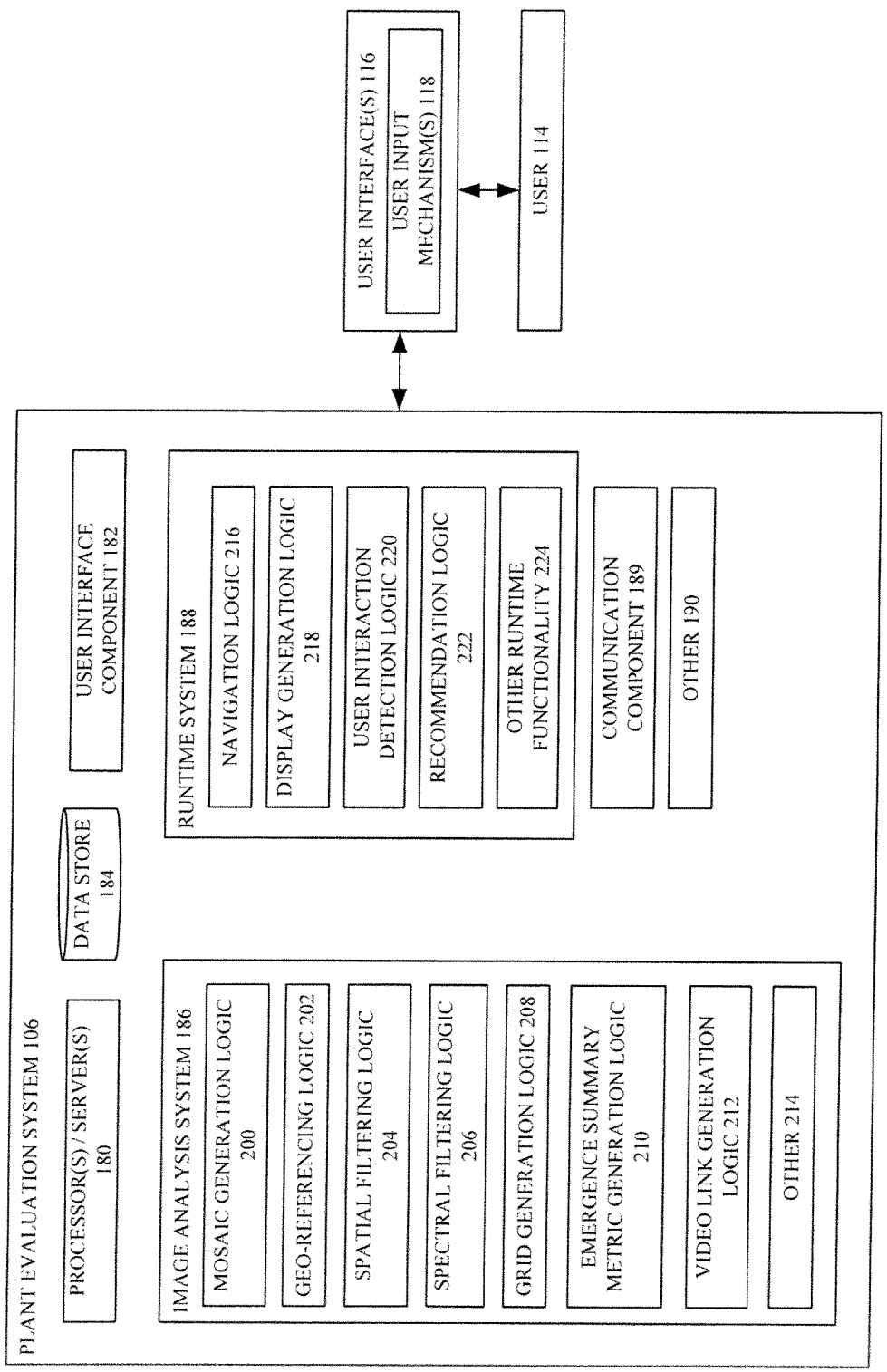
FIG. 2 is one example of a more detailed block diagram of a plant evaluation system.

FIG. 2 shows one example of a more detailed block diagram of plant evaluation system 106. FIG. 2 shows that, in one example, image analysis system 186 illustratively includes mosaic generation logic 200, geo-referencing logic 202, spatial filtering logic 204, and spectral filtering logic 206. It can also include grid generation logic 208, emergence summary metric generation logic 210, video link generation logic 212, and it can include other items 214. Also, in the example shown in FIG. 2, runtime system 188 illustratively includes navigation logic 216, display generation logic 218, user interaction detection logic 220, recommendation logic 222, and it can include a wide variety of other runtime functionality 224.

Figure 3:
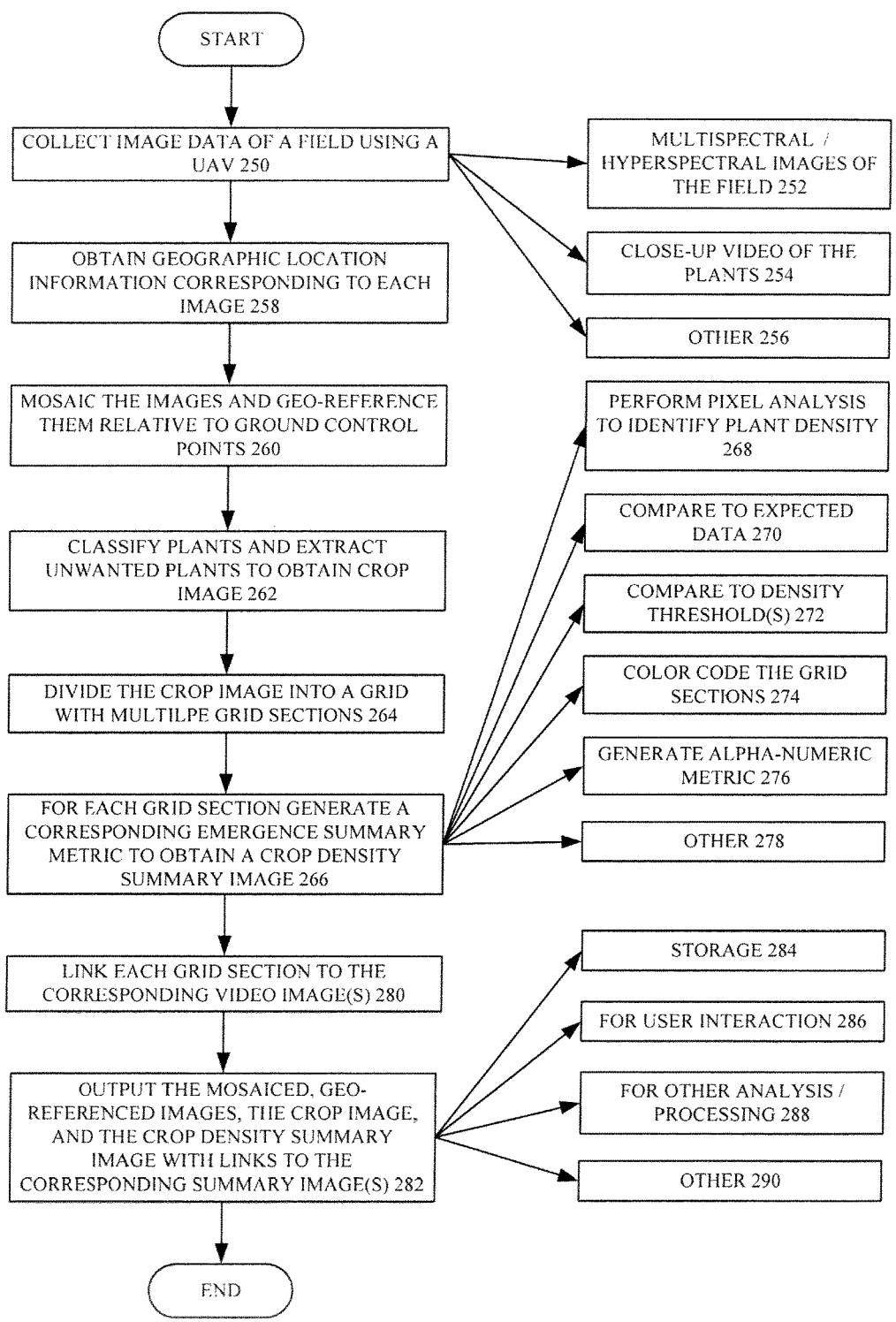
FIG. 3 is a flow diagram illustrating one example of the overall operation of the architecture shown in FIG. 1 in generating a plurality of different crop images.

FIG. 3 is flow diagram illustrating one example of the operation of image analysis system 186 in generating a variety of different images for access by user 114. Unmanned image capture system 102 first collects image data for the field under analysis. This is indicated by block 250 in FIG. 3. As discussed above, this can include multi-spectral or hyperspectral images of the field generated by spectral imaging system 120. This is indicated by block 252 in FIG. 3. It can also include close-up video images of the plants in the field, as generated by video imaging system 122. This is indicated by block 254 in the flow diagram of FIG. 3. The image data can include a wide variety of other image data as well, and this is indicated by block 256.

Geographic location system 124 then obtains geographic location information corresponding to each of the images. This is indicated by block 258. Again, as discussed above, it can include GPS coordinates received by a GPS receiver and corrected by correction information using correction logic 142. It can, of course, include a wide variety of other information as well.

Mosaic generation logic 200 in image analysis system 186 of plant evaluation system 106 then mosaics the images and geo-references them relative to ground control points. This is indicated by block 260 in the flow diagram of FIG. 3. In order to mosaic the images, the geographic location information corresponding to each of the images is used to stitch them together into a larger image of the field under analysis. The geo-referencing logic 202 can automatically geo-reference the image against the ground control points, although this can be done manually as well. This can be done to adjust image alignment or ensure that the mosaicked images are substantially seamlessly stitched together with one another so that no geographic locations are duplicated or skipped in the mosaicked image.

The elements in the mosaicked image are then classified to identify the crop plants and to extract unwanted plants (such as weeds) from the image in order to obtain a crop image. The crop image is illustratively an image that substantially only contains crop plants with weeds being removed. This can be done using both spatial and spectral filtering on the mosaicked image. One example of this is described in greater detail below with respect to FIG. 4. Classifying the plants and extracting the unwanted plants to obtain the crop image is indicated by block 262 in the flow diagram of FIG. 3.

Grid generation logic 208 then divides the crop image into a grid with multiple grid sections. This is indicated by block 264. The grid sections can have any suitable dimensions. In one example, the grid sections may be 5 meters by 5 meters square. This is only one example and a wide variety of other sizes can be used as well.

For each grid section, emergence summary metric generation logic 210 generates a corresponding emergence summary metric that is indicative of an emergence characteristic of the crop plants, in that grid section. This obtains a crop density summary image that shows the various emergence summary metrics for the different grid sections for the image. This is indicated by block 266. This can be done in a variety of different ways. For instance, spectral analysis can be performed on the image within each grid section to identify a number of pixels in the image that correspond to crop plants. This can be used to identify a crop plant density within each grid section. This is indicated by block 268. The density can then be compared to expected density data that indicates an expected crop plant density within a grid section of that size, in that field. This is indicated by block 270. The comparison can generate a result that indicates whether the actual crop density is the same, above, or below the expected crop density value. This metric can indicate whether the emergence rate of the plants in that grid section is above, roughly equal to, or below the expected emergence rate.

In another example, the crop density value can be compared to one or more different density threshold values. This is indicated by block 272. The result of that comparison can be used to generate the emergence summary metric for that grid section. The various grid sections can then be color-coded based upon the emergence summary metric corresponding to each of the grid sections. This is indicated by block 274. For instance, a grid section that has an emergence metric that is above an expected value may have one color, while a grid section which has an emergence metric that is approximately equal to the expected value may have a second color, and a grid section that has an emergence metric below the expected value may have a third color. In addition, those grid sections where substantially no crop plants have emerged may have yet a different color. Further, in the example where the crop density metric is compared against various different threshold values, the grid section can be color-coded based upon where the observed crop density falls relative to the threshold values. Also, the grid sections need not be color-coded, but may have a different visual indicator applied to them indicating the crop density metric. For instance, those that have a crop density that is approximately equal to an expected crop density may simply be statically displayed. However, those that have a crop density below the expected level may be dynamic (such as flashing at a first rate) while those that have a crop density higher than the expected value may be dynamic in a different way (such as flashing at a second rate). Similarly, other visual indicia may be used. For example, some grid sections may be bolded or outlined in a heavy outline, or otherwise visually distinguished from the other grid sections. These are examples only, and a wide variety of other visual indicia can be used.

Also, in one example, each grid section has an alpha-numeric metric value generated therefore. This is indicated by block 276. For instance, if the grid section has a crop density that exceeds the expected crop density, an alpha-numeric display of ">100%" may be displayed on that grid section. If it has a crop density that is below the expected value, then an alpha-numeric value of "<100%" may be displayed on that grid section, etc. Again, these are only examples of different alpha-numeric metric values that can be generated for, and displayed on, each grid section. A wide variety of other emergence summary metrics can be generated for the grid sections, and this is indicated by block 278.

Video link generation logic 212 then generates a link, for each grid section. The link links a corresponding grid section with the video image for that grid section generated by video imaging system 122. This is indicated by block 280. For instance, video link generation logic 212 can access the geographic location information corresponding to each individual grid section, and can find the video image that has the same corresponding geographic location information. The link generation logic 212 can then generate an actuatable link from the grid section, in a grid section display, to the video. Therefore, when the user actuates a grid section, in the grid section display, this can activate the link so that the corresponding video image can be displayed to the user. This allows the user to evaluate the veracity of the emergence summary metric and to get an actual view of the crop plants in order to perform that evaluation.

Communication component 189 can then output the mosaicked, geo-referenced images, the crop image (that shows the crop plants) and the crop density summary image (that shows the grid sections and the corresponding emergence summary metrics) along with the links to the corresponding summary images, to other systems. This is indicated by block 282. In one example, it can be output to a remote system 108 for storage in a corresponding data store 172. This is indicated by block 284. It can be output using a user interface 116, for user interaction by a user 114. This is indicated by block 286. It can be output for other analysis or for further processing at a wide variety of other systems or machines as well. This is indicated by block 288. For instance, it can be output to a machine that is applying fertilizer to indicate whether, at each grid section, the machine should apply fertilizer, whether it should apply extra fertilizer, whether it should not apply any fertilizer, etc. The information can be used to generate crop or field treatment recommendations or it can be output in a variety of other ways as well, and this is indicated by block 290.

Figure 4:
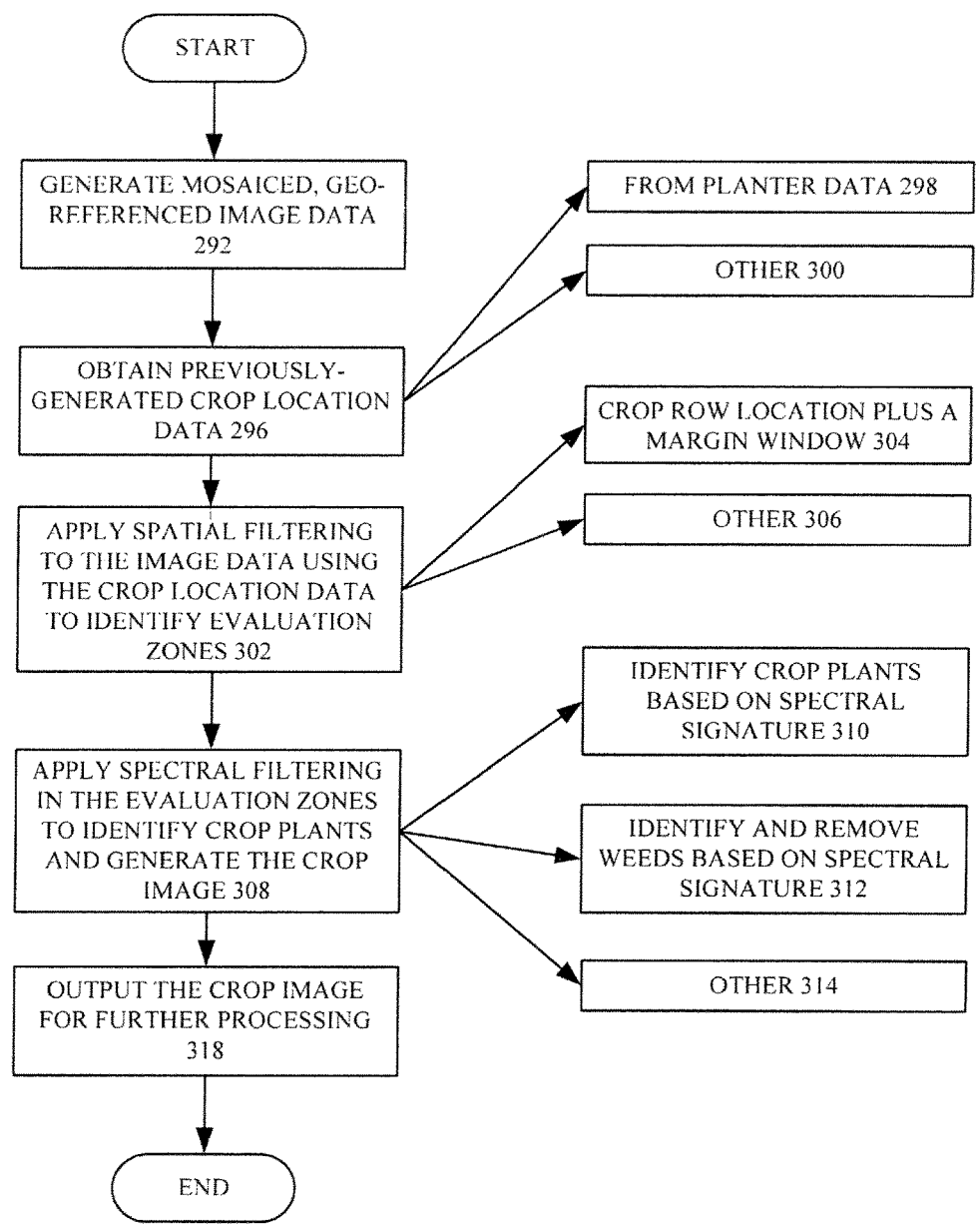
FIG. 4 is a flow diagram illustrating one example of the operation of the plant analysis system in applying spatial and spectral filtering to obtain a crop image.
Figure 4A:
FIGS. 4A-4C show examples of user interface displays that can be generated by the plant evaluation system.
Figure 4B:
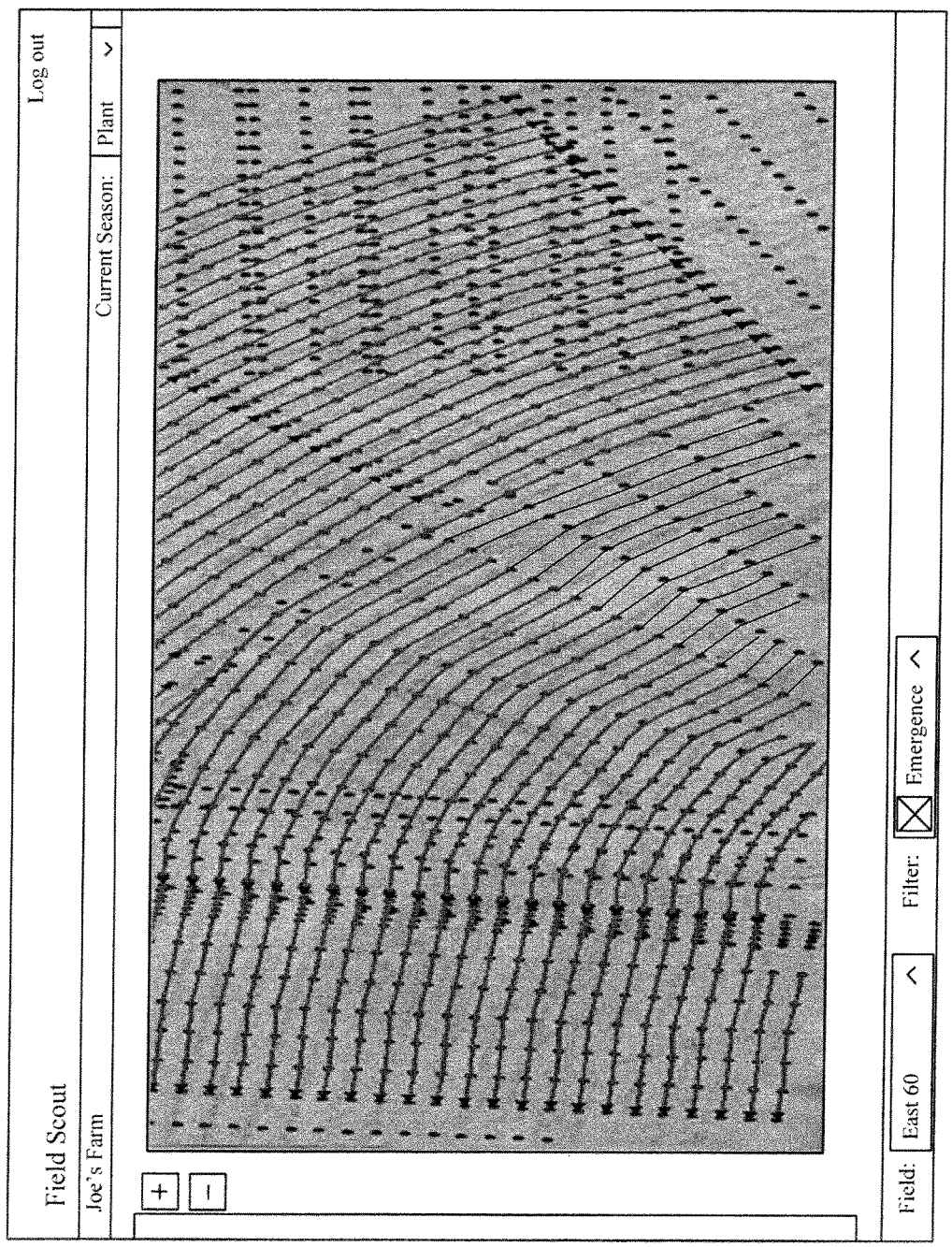
Figure 4C:
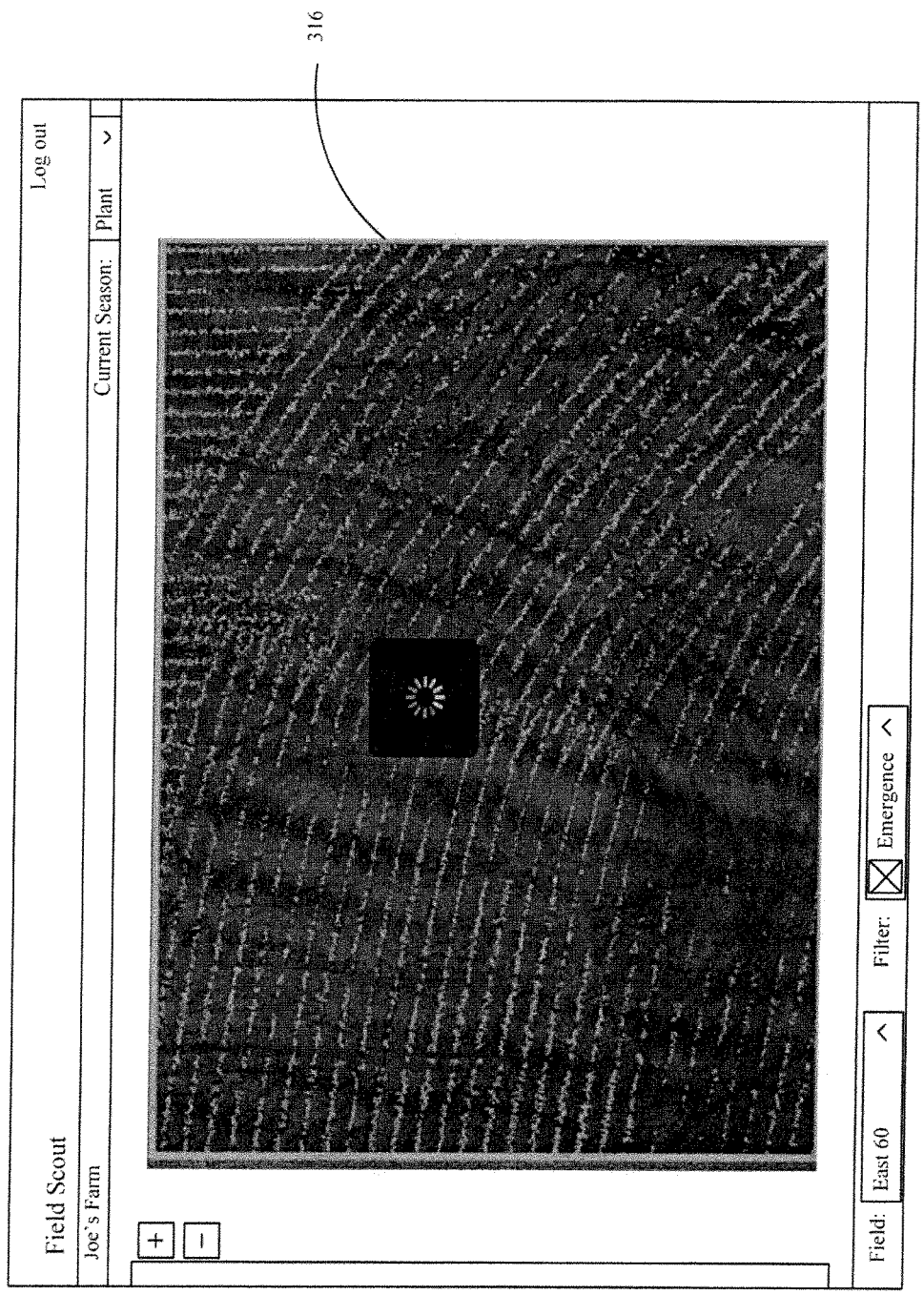

FIG. 4 is a flow diagram illustrating one example of how the mosaicked, geo-referenced image is classified to generate the crop image. Recall that the crop image shows substantially only crop plants so that the crop density, or other emergence characteristic, can be obtained. FIGS. 4A-4C show various images. FIGS. 4-4C will now be described in conjunction with one another.

Mosaic generation logic 200 and geo-referencing logic 202 are first used to generate the mosaicked, geo-referenced image data for the field under analysis. This is indicated by block 292 in FIG. 4. FIG. 4A shows one example of a mosaicked, geo-referenced, spectral image 294 for a given field of interest. It can be seen that the crop rows are roughly distinguishable in the spectral image 294.

Spatial filtering logic 204 then obtains the previously-generated crop location data which provides a geographic location of the rows of crop plants (or the plants themselves). This is indicated by block 296. FIG. 4B shows one example of a display showing the geographic location of the crops based on the previously-generated crop location data. As discussed above, this can be previously-generated information, that is generated using a planting machine 104. This is indicated by block 298 in the flow diagram of FIG. 4. Of course, the crop location data can be obtained from other sources as well, and this is indicated by block 300.

Spatial filtering logic 204 then applies spatial filtering to the spectral image using the crop location data in order to identify evaluation zones that will be used to evaluate a crop emergence characteristic (such as crop density). Applying the spatial filtering is indicated by block 302. In one example, the crop location data identifies the geographic location of the crop rows. Therefore, spatial filtering logic 204 identifies a reference line corresponding to the center of each crop row, and also identifies a margin window around that reference line, for each row. The margin window identifies an evaluation zone for a given row. It is assumed that anything growing between two adjacent evaluation zones (for two adjacent crop rows) is a plant that is growing between the rows and therefore is very likely a weed or some other undesirable plant. Thus, the evaluation zones identify a zone for spectral filtering for each crop row. The spectral filtering need not be performed on any portion of the images, other than within the evaluation zones. Identifying an evaluation zone as a crop row location plus a margin window around the crop row location is indicated by block 304 in FIG. 4. The spatial filtering can be applied in other ways to identify evaluation zones, and this is indicated by block 306.

Spectral filtering logic 206 then applies spectral filtering in the evaluation zones to evaluate crop plants within those evaluation zones, and to generate the crop image, which substantially shows only crop plants in the spectral image. This is indicated by block 308. In one example, spectral filtering logic 206 identifies pixels, within the evaluation zones defined in the spectral image, that have a spectral signature that corresponds to the crop plants. The crop plants will have a spectral signature that differs from that of soil, and from that of a variety of different types of weeds. Therefore, by filtering the data in the evaluation zones in the spectral image to only show plants with a spectral signature corresponding to a crop plant, the crop image can be obtained. Identifying crop plants based on spectral signature is indicated by block 310. Identifying and removing weeds based upon their spectral signature is indicated by block 312. The crop image can be generated in other ways as well, and this indicated by block 314.

FIG. 4C shows one example of a crop image 316. It can be seen that image 316 differs from image 294 (shown in FIG. 4A). Image 316 more clearly shows only crop plants in rows, and the spectral information corresponding to weeds or other plants has been filtered out based on the crop location data (e.g., as shown in FIG. 4B). The crop image can then be output for further processing (such as to identify grid sections with various crop density metrics, etc.). This is indicated by block 318 in FIG. 4.

Figure 5:
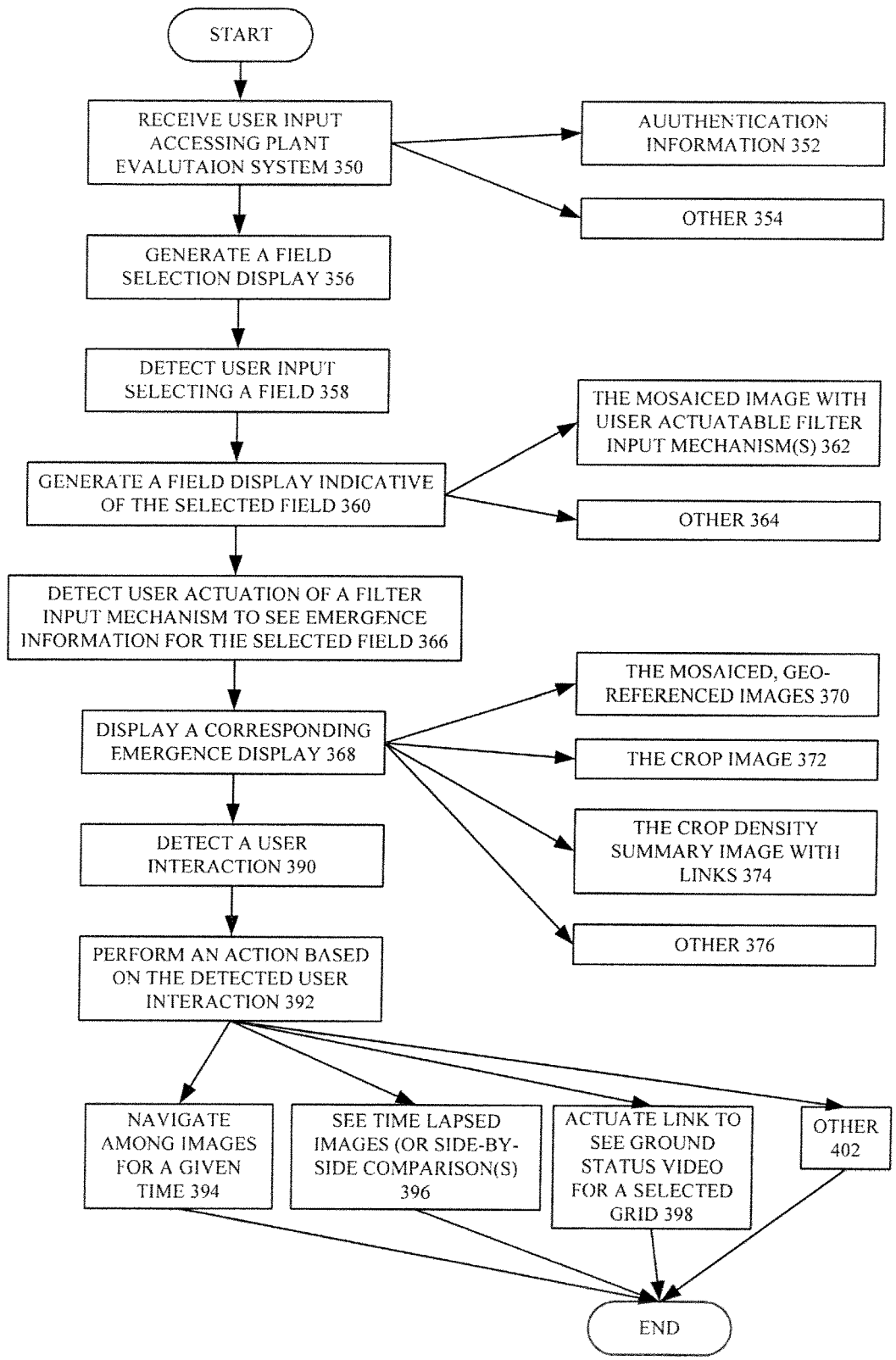
FIG. 5 is a flow diagram illustrating one example of the operation of a runtime system.
Figure 5A:
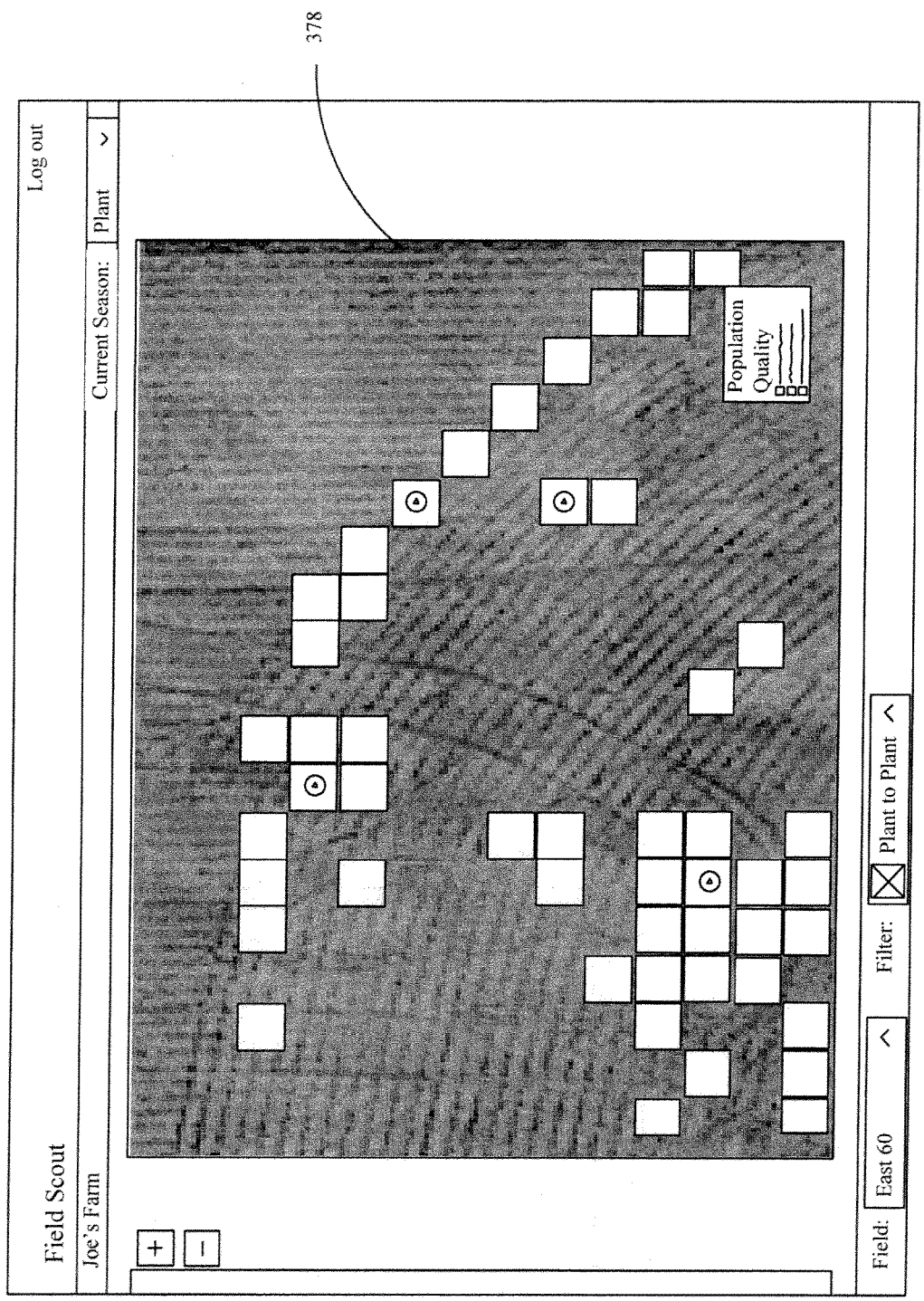
Figure 5B:
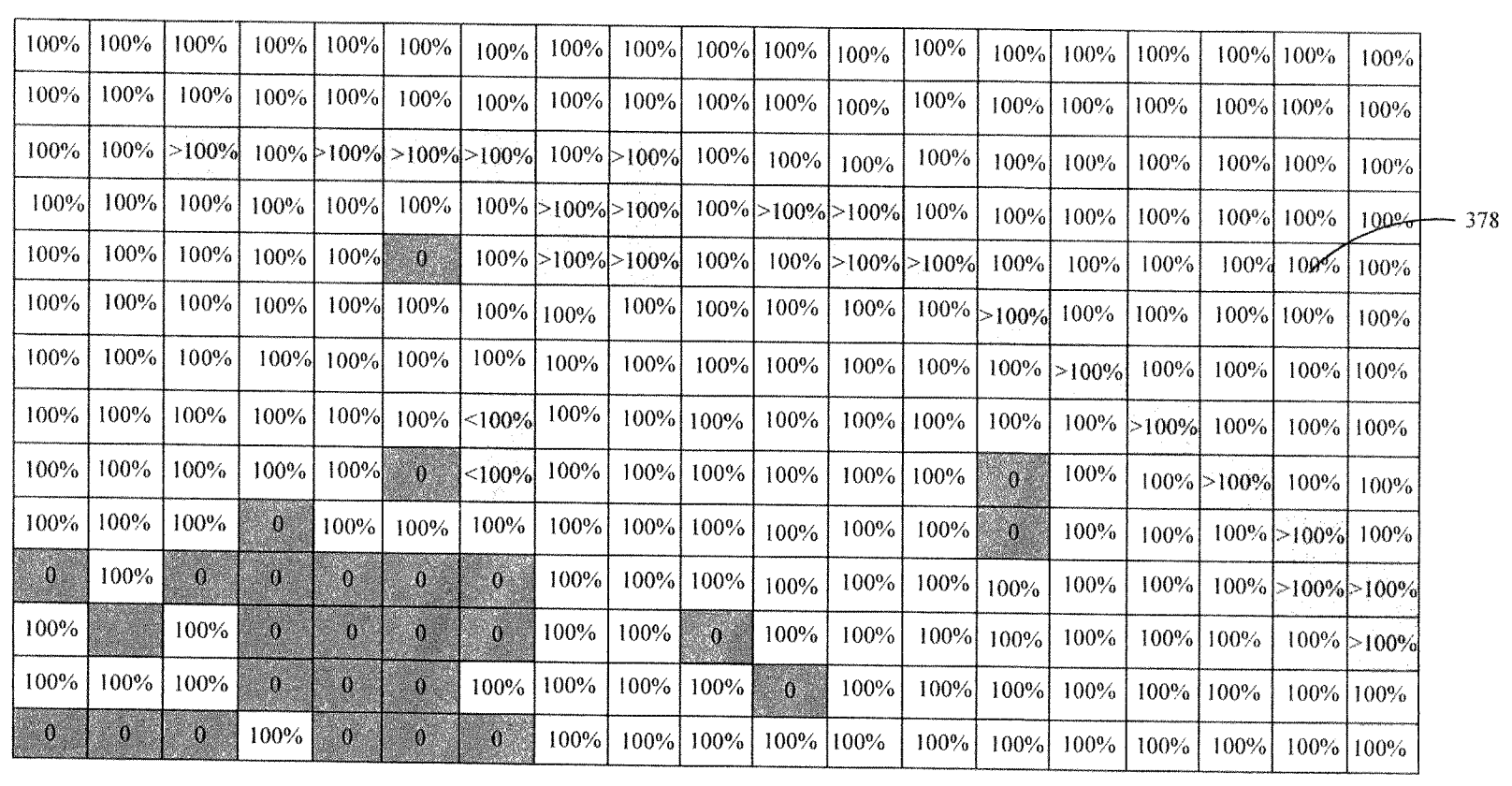
Figure 5C:
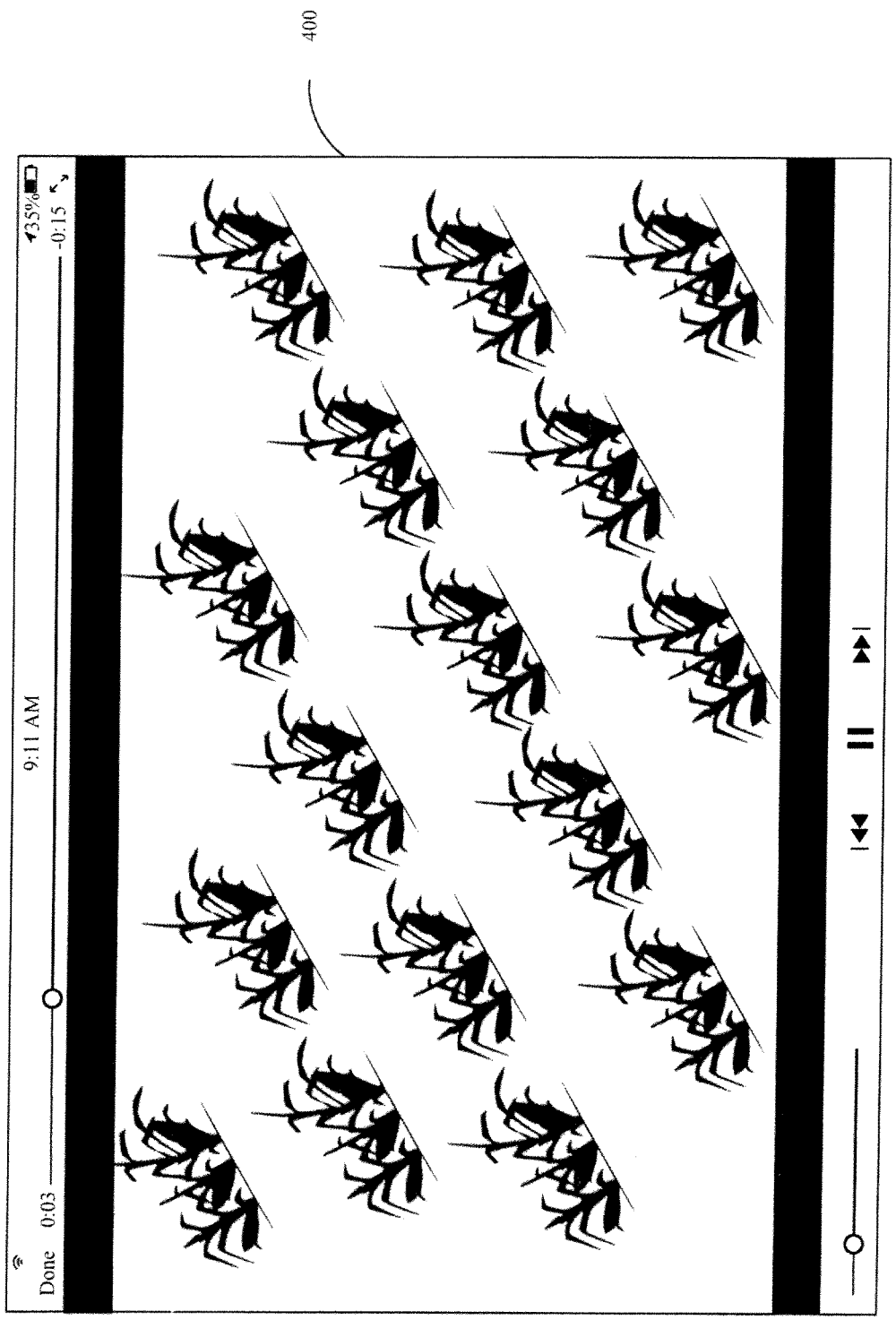

FIG. 5 is a flow diagram illustrating one example of the operation of runtime system 188 in plant evaluation system 106. FIGS. 5A-5C show various user interface displays that can be generated during runtime, although other or different displays can be generated as well. FIGS. 5-5C will now be described in conjunction with one another.

Runtime system 188 first receives a user input from user 114 indicating that the user wishes to access the plant evaluation system 106. This is indicated by block 350 in FIG. 5. For instance, the user can input authentication information 352 or provide the user input in other ways 354. Display generation logic 218 then generates a field selection display with a set of user input mechanisms. In one example, the user can actuate one of the user input mechanisms to select a field for which information is to be accessed. Generating the field selection user interface display is indicated by block 356.

User interaction detection logic 220 then detects a user input selecting a field. This is indicated by block 358. Display generation logic 218 then generates a field display indicative of the selected field. This is indicated by block 360. The field display can take a wide variety of different forms. In one example, it is the mosaicked image of the selected field, along with user actuatable filter input mechanisms that allow the user to filter that input to see a variety of different information corresponding to the selected field. This is indicated by block 362. Of course, it can be any other display for the field as well, and this is indicated by block 364.

User interaction detection logic 220 then detects user actuation of a filter input mechanism to see emergence information for the selected field. This is indicated by block 366.

In response, display generation logic 218 can access any of the various displays or images that were generated by image analysis system 186, that are indicative of plant emergence in the selected field. That image can be referred to as the emergence display. This is indicated by block 368. For instance, it can be the mosaicked, geo-referenced images, as indicated by block 370. It can be the crop image (such as that shown in FIG. 4B) as indicated by block 372. It can be a crop density summary image with links to the underlying video images. This is indicated by block 374. It can also be other images as well, as indicated by block 376.

FIG. 5A shows one example of a crop density summary image 378. It can be seen that the image 378 has grid sections defined by the squares on the image. The grid sections can each have one of a plurality of different colors based upon their corresponding emergence summary metric. For instance, a first color (e.g., green) grid section can indicate that the crop density is at an expected level in that grid section. A second color (e.g., red) grid section may indicate that the crop density level is either zero or below a given threshold, and a third color grid section can indicate that the crop density is somewhere between an expected level and the lower threshold. A different color may indicate that the crop density in the corresponding grid section is above an expected level, or that it is at some other level. FIG. 5B shows a second example of a crop density summary image.

FIG. 5B shows that the underlying crop image has been removed and replaced by the grid sections. Thus, the grid sections shown in FIG. 5B also have alphanumeric metrics displayed on them. The metrics are illustratively crop density metrics indicative of the crop density in the corresponding grid sections. Again, the grid sections can also be color-coded to indicate where the crop density falls relative to expected data or various crop density thresholds.

Once the emergence display is displayed (such as the crop density displays shown in FIGS. 5A and 5B) the user can, in one example, interact with those images. For instance, each of the grid sections may be an actuatable link. In another example, the displayed image is associated with a time lapse mechanism that the user can actuate to show corresponding images that were generated earlier or later in time from the currently displayed images. All of these and other examples of user input mechanisms can be used.

For instance, in one example, user interaction detection logic 220 detects a user interaction with the displayed emergence display. This is indicated by block 390 in the flow diagram of FIG. 5. Runtime system 188 then performs an action based upon the detected user interaction. This is indicated by block 392. The actions can take a wide variety of different forms. For instance, in one example, navigation logic 216 navigates among images that were taken at a particular time. The images may be different portions of the field under analysis, or they may be for different fields. Navigating among different images is indicated by block 394. In another example, the action may be to display time lapsed images (or to display them side-by-side with one another) based upon the user interaction. This is indicated by block 396. For instance, if a user is viewing the crop emergence display, but a plurality of different crop emergence displays have been generated over time, the user may actuate a user input mechanism (such as by moving a slider on the display) to advance either forward or backward in time between the newest, and oldest, emergence density images. The time lapsed images can be displayed in other ways as well.

Further, each grid section may be an actuatable link that, when actuated by the user, navigates the user to the underlying video image for that corresponding grid section. Actuating the link to see the ground status video for a selected grid section is indicated by block 398.

FIG. 5C shows one example of a video image. In the example shown in FIG. 5C, image 400 illustratively corresponds to a grid section on the display of either FIG. 5A or 5B. When the user actuates the grid section, the user can see the corresponding video image to verify the veracity of the emergence metric that is displayed in that grid section.

The actions that are performed based on detected user interactions can take a wide variety of other forms as well. This is indicated by block 402.

It can thus be seen that the present system provides a number of advantages. Applying spatial filtering based on plant row locations (or individual plant locations) increases the speed and efficiency in the processing. Evaluation zones can be identified around the plant row locations so that spectral filtering only needs to be performed within those zones instead of for the entire image. Generating an emergence metric, and color-coding or otherwise providing visual indicia indicative of where that metric falls with respect to an expected value, also surfaces relevant information much more quickly. This can reduce the network bandwidth requirement and other processing loads on the system. In addition, by downloading these metrics to other agricultural machines, site-specific treatment can be performed quickly, easily, and efficiently. Actions can be taken based upon the plant emergence metric to save chemicals, to save time, and to otherwise improve the site-specific farming.

It will be noted that the above discussion has described a variety of different systems, components and/or logic. It will be appreciated that such systems, components and/or logic can be comprised of hardware items (such as processors and associated memory, or other processing components, some of which are described below) that perform the functions associated with those systems, components and/or logic. In addition, the systems, components and/or logic can be comprised of software that is loaded into a memory and is subsequently executed by a processor or server, or other computing component, as described below. The systems, components and/or logic can also be comprised of different combinations of hardware, software, firmware, etc., some examples of which are described below. These are only some examples of different structures that can be used to form the systems, components and/or logic described above. Other structures can be used as well.

The present discussion has mentioned processors and servers. In one example, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 6:
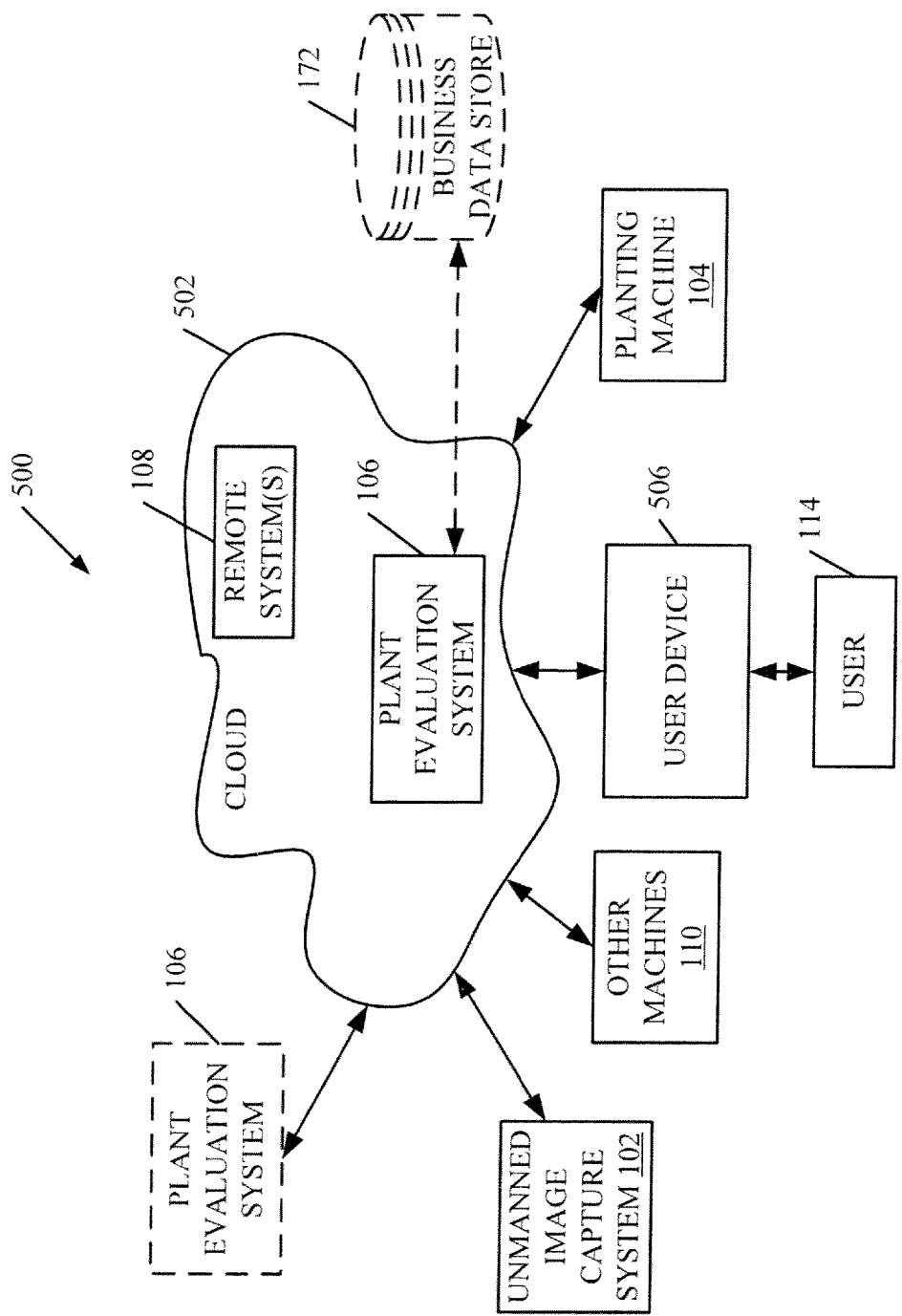
FIG. 6 is a block diagram of one example of the architecture illustrated in FIG. 1, deployed in a remote server architecture.

FIG. 6 is a block diagram of architecture 100, shown in FIG. 1, except that it is deployed in a remote server architecture 500. In an example, remote server architecture 500 can provide computation, software, data access, and storage services that do not require end-user knowledge of the physical location or configuration of the system that delivers the services. In various embodiments, remote servers can deliver the services over a wide area network, such as the internet, using appropriate protocols. For instance, remote servers can deliver applications over a wide area network and they can be accessed through a web browser or any other computing component. Software or components shown in FIG. 1 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 6, some items are similar to those shown in FIG. 1 and they are similarly numbered. FIG. 6 specifically shows that remote systems 108 and plant evaluation system 106 can be located at a remote server location 502. The information can be provided to remote server location 502 by unencumbered image capture system 102 and planting machine 104 in any of a wide variety of different ways. Therefore, user 114 and machines 110 can access those systems through remote server location 502. This can be done using a user device 506, for instance.

FIG. 6 also depicts another embodiment of a remote server architecture. FIG. 6 shows that it is also contemplated that some elements of FIG. 1 are disposed at remote server location 502 while others are not. By way of example, data store 172 or plant evaluation system 106 can be disposed at a location separate from location 502, and accessed through the remote server at location 502. Regardless of where they are located, they can be accessed directly by user device 506, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an embodiment, where cell coverage is poor or nonexistent, another mobile machine (such as a fuel truck) can have an automated information collection system. As the harvester comes close to the fuel truck for fueling, the system automatically collects the information from the harvester using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the harvester until the harvester enters a covered location. The harvester, itself, can then send the information to the main network.

It will also be noted that the elements of FIG. 1, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 7:
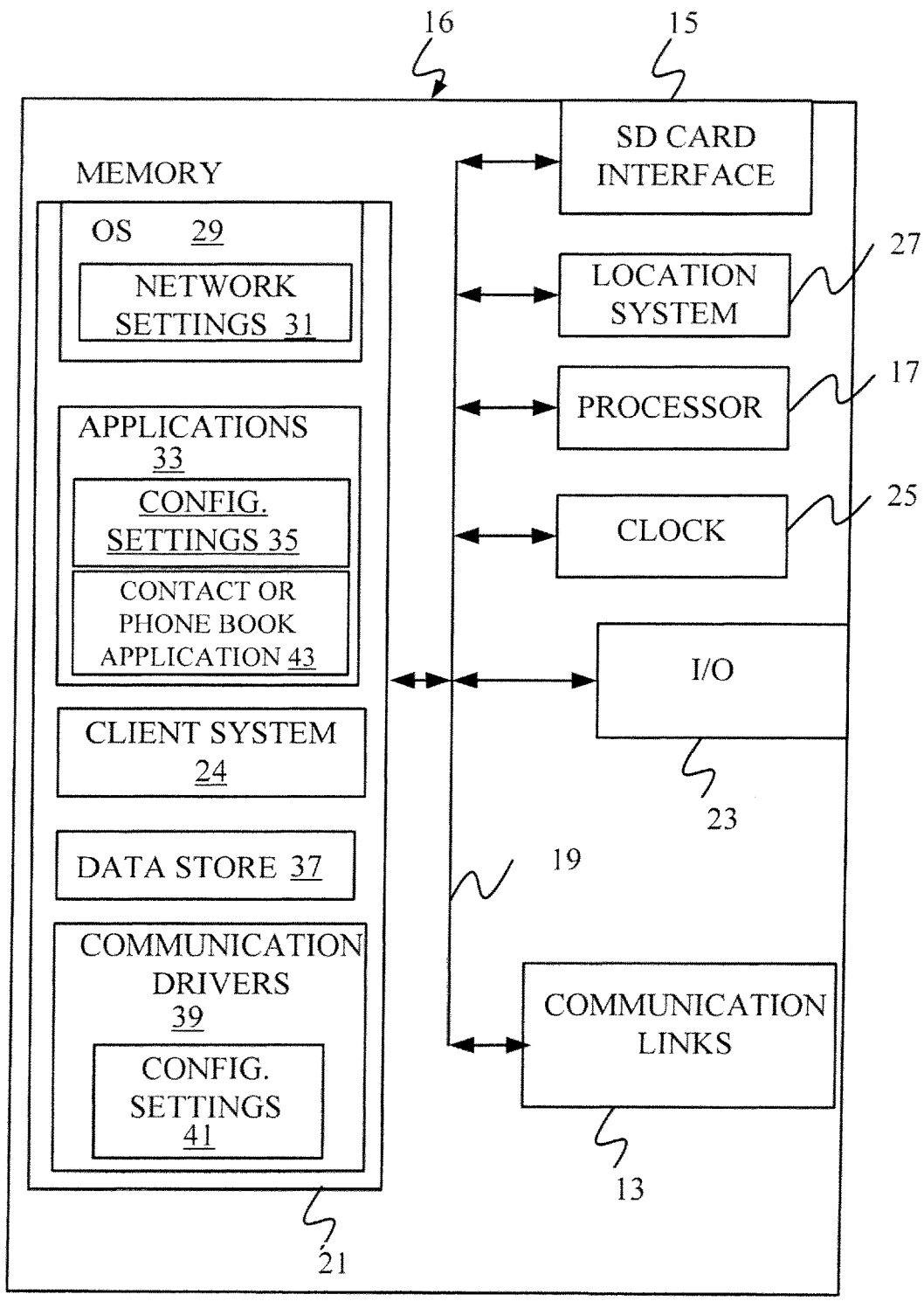
FIGS. 7-9 are examples of mobile devices that can be used in the architectures illustrated in the previous figures.
Figure 8:
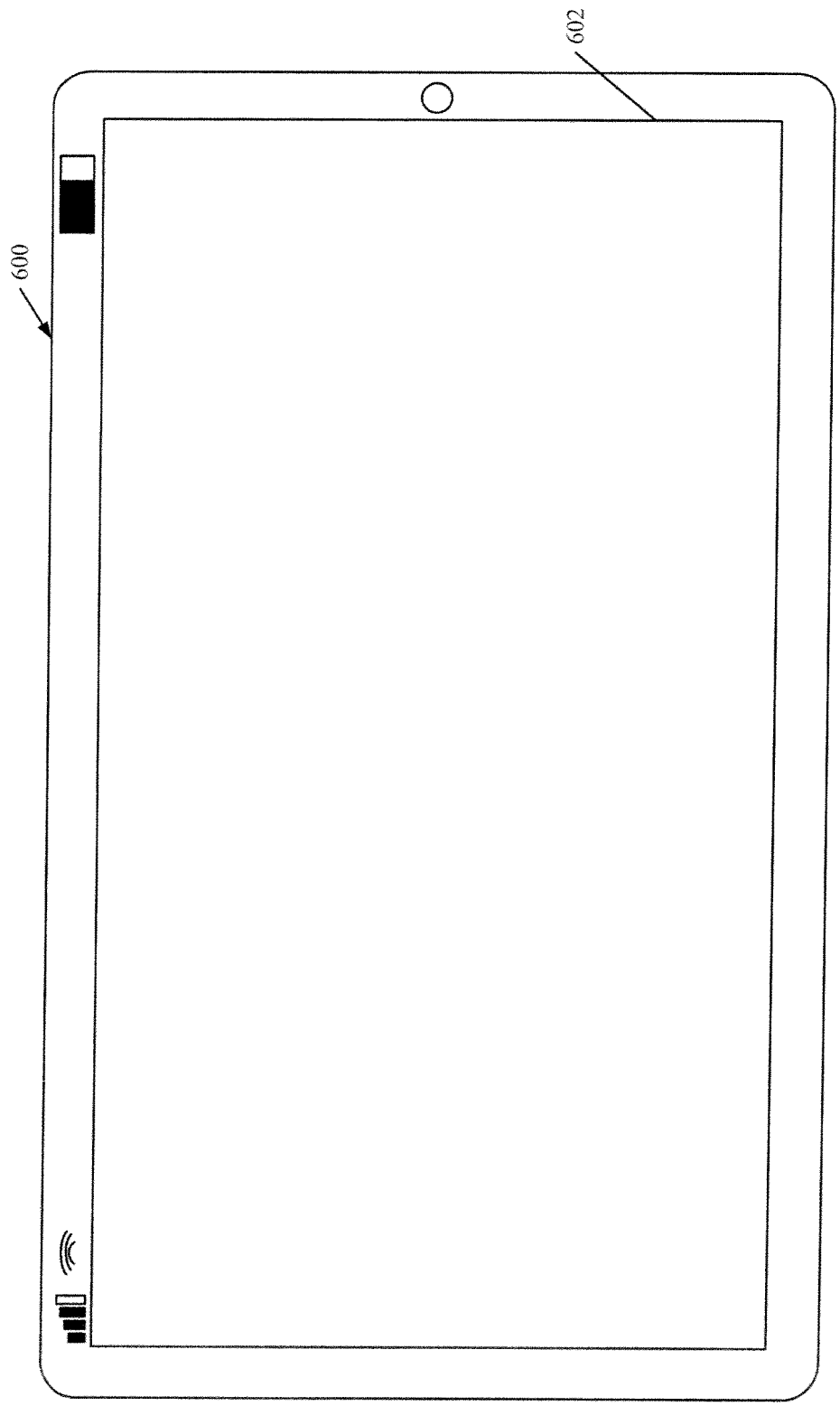
Figure 9:
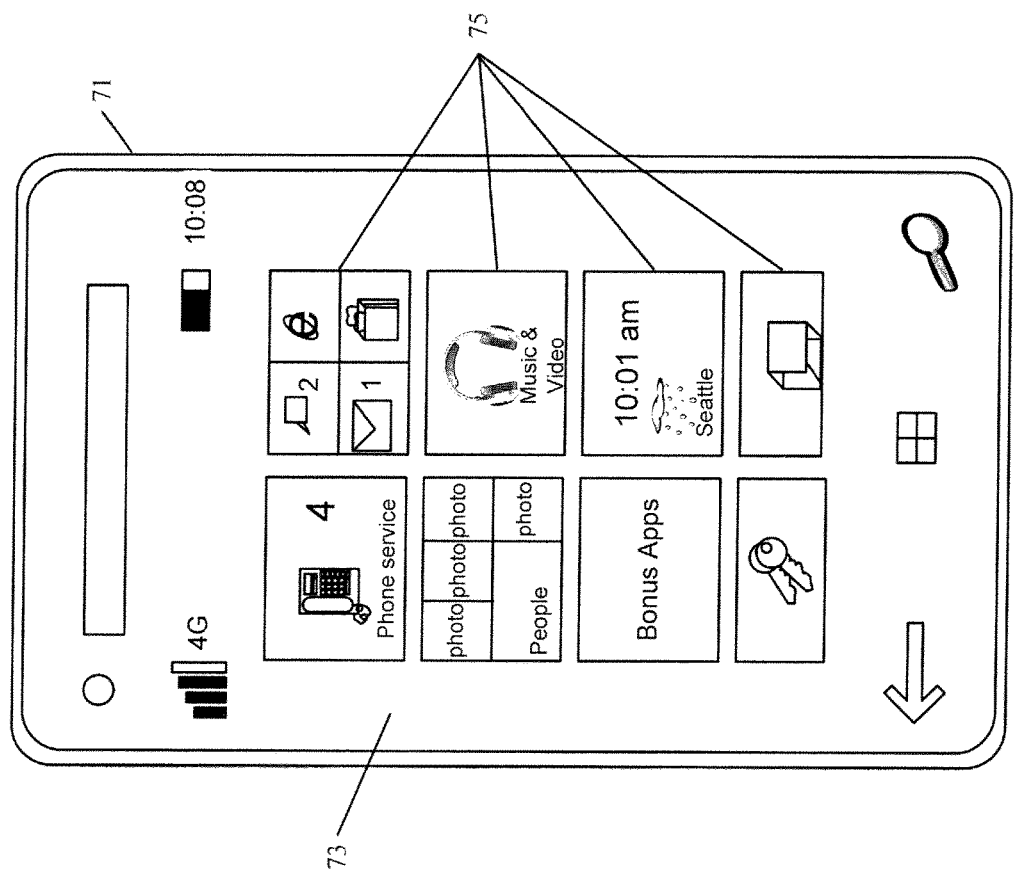

FIG. 7 is a simplified block diagram of one illustrative example of a handheld or mobile computing device that can be used as a user's or client's hand held device 16, in which the present system (or parts of it) can be deployed. For instance, a mobile device can be deployed in the operator compartment of machines 104 and 110, or as user device 506 for use in generating, processing, or displaying the plant evaluation information. FIGS. 8-9 are examples of handheld or mobile devices.

FIG. 7 provides a general block diagram of the components of a client device 16 that can run some components shown in FIG. 1, that interacts with them, or both. In the device 16, a communications link 13 is provided that allows the handheld device to communicate with other computing devices and under some embodiments provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody any processor or server from previous Figures) along a bus 19 that is also connected to memory 21 and input/output (I/O) components 23, as well as clock 25 and location system 27.

I/O components 23, in one embodiment, are provided to facilitate input and output operations. I/O components 23 for various embodiments of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 8 shows one embodiment in which device 16 is a tablet computer 600. In FIG. 8, computer 600 is shown with user interface display screen 602. Screen 602 can be a touch screen or a pen-enabled interface that receives inputs from a pen or stylus. It can also use an on-screen virtual keyboard. Of course, it might also be attached to a keyboard or other user input device through a suitable attachment mechanism, such as a wireless link or USB port, for instance. Computer 600 can also illustratively receive voice inputs as well.

FIG. 9 shows that the device can be a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 10:
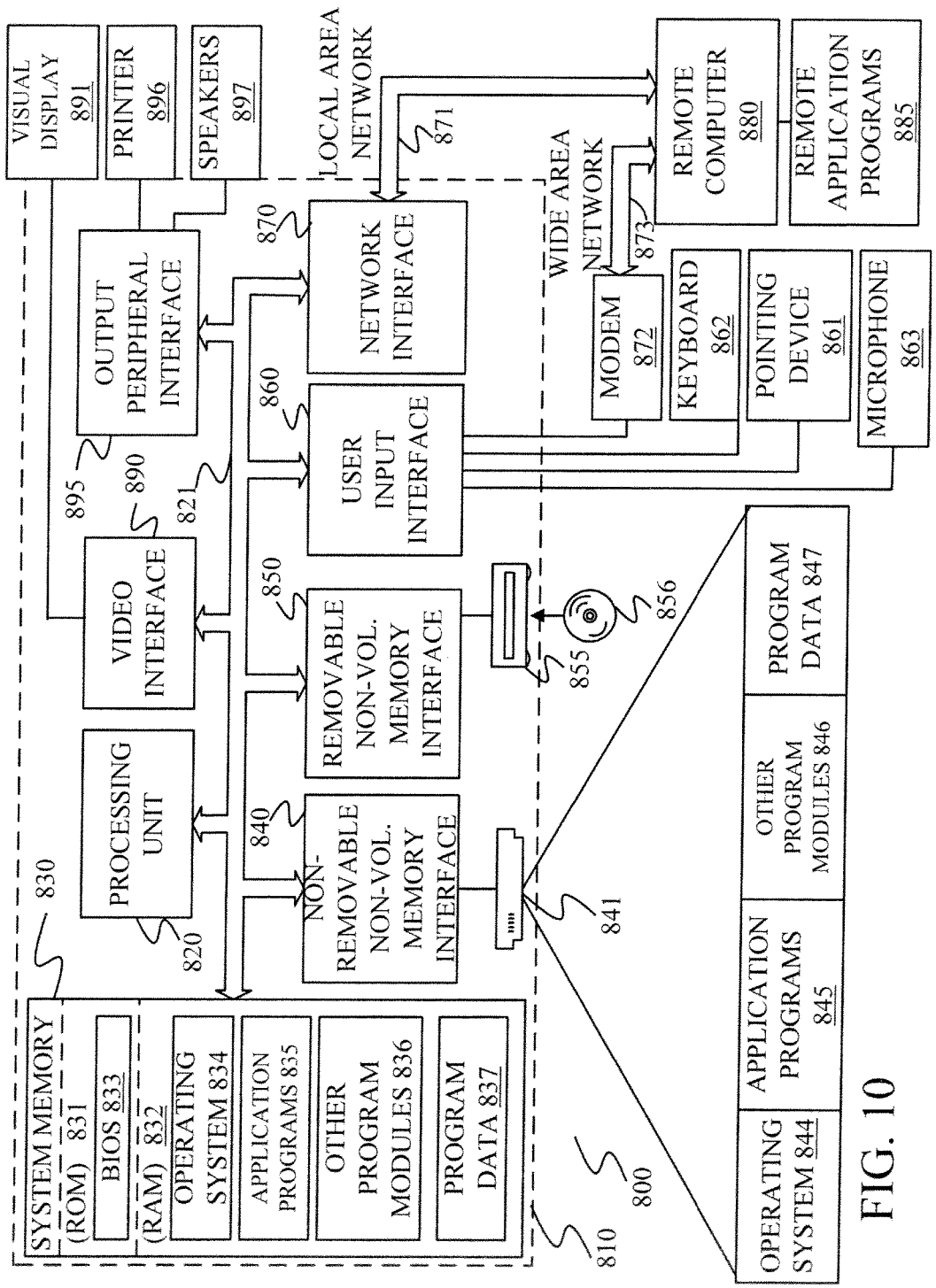
FIG. 10 is a block diagram of one example of a computing environment that can be used in the architectures shown in the previous figures.

FIG. 10 is one example of a computing environment in which elements of FIG. 1, or parts of it, (for example) can be deployed. With reference to FIG. 10, an example system for implementing some embodiments includes a general-purpose computing device in the form of a computer 810. Components of computer 810 may include, but are not limited to, a processing unit 820 (which can comprise processors or servers from any previous Figure), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 1 can be deployed in corresponding portions of FIG. 10.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable volatile/nonvolatile computer storage media. By way of example only, FIG. 10 illustrates a hard disk drive 841 that reads from or writes to non-removable, nonvolatile magnetic media, nonvolatile magnetic disk 852, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers

897 and printer 896, which may be connected through an output peripheral interface 895.

The computer 810 is operated in a networked environment using logical connections (such as a local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 10 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is a computing system, comprising:
spatial filtering logic that receives image data indicative of an image of a field and crop location data indicative of a geographic location of crops in the field and identifies a crop evaluation zone, on the image, based on the crop location data; and emergence metric generation logic that generates an emergence metric indicative of an emergence characteristic of the crops in the crop evaluation zone in the field, based on spectral image data corresponding to the crop evaluation zone in the image.

Example 2 is the computing system of any or all previous examples wherein the crop location data identifies a geographic location of where crop rows were planted in the field and wherein the spatial filtering logic identifies a row level crop evaluation zone for each crop row in the field, each row level crop evaluation zone defining a window around the geographic location of where a corresponding crop row was planted in the field.

Example 3 is the computing system of any or all previous examples and further comprising: spectral filtering logic that filters spectral information in the row level crop evaluation zones to identify a crop density in the row level crop evaluation zones.

Example 4 is the computing system of any or all previous examples wherein the spectral filtering logic confines the filtering of the spectral information to the spectral information in the crop evaluation zones.

Example 5 is the computing system of any or all previous examples and further comprising:
grid generation logic that divides the image of the field into a grid with grid sections, each grid section corresponding to a geographic area in the field.

Example 6 is the computing system of any or all previous examples wherein the emergence metric generation logic generates an emergence metric, indicative of an emergence characteristic, corresponding to each grid section in the grid.

Example 7 is the computing system of any or all previous examples and further comprising:
a runtime system that detects a user request input and generates a crop display that visually displays the grid sections and visual indicia indicative of the corresponding emergence metrics.

Example 8 is the computing system of any or all previous examples wherein the runtime system displays color coded grid sections as the visual indicia corresponding to the emergence metric for each grid section.

Example 9 is the computing system of any or all previous examples wherein the runtime system displays alphanumeric information on each of the grid sections as the visual indicia corresponding to the emergence metric for each grid section.

Example 10 is the computing system of any or all previous examples and further comprising:
video link generation logic that generates a user actuatable link, for each given grid section, the user actuatable link linking to a video image of the field, corresponding to the given grid section.

Example 11 is a method, comprising:
receiving a field image of a field;
receiving crop location data indicative of a geographic location of crops in the field;
identifying a crop evaluation zone, on the image, based on the crop location data;
performing spectral filtering on the crop evaluation zone to identify crops in the crop evaluation zone; and
generating an emergence metric indicative of an emergence characteristic of the identified crops in the crop evaluation zone; and
generating a user interface indicative of the emergence metric visually corresponding to the crop evaluation zone.

Example 12 is the method of any or all previous examples wherein the crop location data identifies a geographic location of where crop rows were planted in the field and wherein identifying a crop evaluation zone comprises:
identifying a row level crop evaluation zone for each crop row in the field, each row level crop evaluation zone defining a window around the geographic location of where a corresponding crop row was planted in the field.

Example 13 is the method of any or all previous examples wherein performing spectral filtering comprises:
filtering spectral information in the row level crop evaluation zones to identify a crop density in the row level crop evaluation zones.

Example 14 is the method of any or all previous examples and further comprising:
dividing the image of the field into a grid with grid sections, each grid section corresponding to a geographic area in the field, wherein generating an emergence metric includes generating an emergence metric, indicative of an emergence characteristic, corresponding to each grid section in the grid.

Example 15 is the method of any or all previous examples and further comprising:
detecting a user request input; and
generating a crop display that visually displays the grid sections and visual indicia indicative of the corresponding emergence metrics.

Example 16 is the method of any or all previous examples wherein generating a crop display comprises:
generating color coded grid sections as the visual indicia corresponding to the emergence metric for each grid section.

Example 17 is the method of any or all previous examples wherein generating a crop display comprises:
generating alphanumeric information on each of the grid sections as the visual indicia corresponding to the emergence metric for each grid section.

Example 18 is the method of any or all previous examples wherein generating a crop display comprises:

generating a user actuatable link, for each given grid section, the user actuatable link being actuated to navigate to a video image of the field, corresponding to the given grid section.

Example 19 is a computing system, comprising:

spatial filtering logic that receives image data indicative of an image of a field and crop location data indicative of a geographic location of where crop rows were planted in the field, and that identifies a row level crop evaluation zone for each crop row in the field, each row level crop evaluation zone defining a window around the geographic location of where a corresponding crop row was planted in the field;

spectral filtering logic that filters spectral information in the row level crop evaluation zones to identify a crop density in the row level crop evaluation zones;

grid generation logic that divides the image of the field into a grid with grid sections, each grid section corresponding to a geographic area in the field;

emergence metric generation logic that logic generates an emergence metric, indicative of an emergence characteristic, corresponding to each grid section in the grid; and a user interface component that generates a crop display that visually displays the grid sections and visual indicia indicative of the corresponding emergence metrics.

Example 20 is the computing system of any or all previous examples and further comprising:

video link generation logic that generates a user actuatable link, for each given grid section, the user interface component displaying the user actuatable link for each given grid section on the given grid section on the on the crop display, each link being actuatable to navigate to a video image of a portion of the field, corresponding to the given grid section.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computing system, comprising:
    a communication component that receives pre-determined crop location data generated when the crop was planted and being indicative of a geographic location where a plurality of different crop rows were planted by a planter in a field;
    spatial filtering logic that receives image data indicative of an image of the field and the pre-determined crop location data and that identifies a crop evaluation zone, corresponding to each of the plurality of different rows, on the image, based on the crop location data; and
    emergence metric generation logic that generates an emergence metric indicative of an emergence characteristic of the crops in each crop evaluation zone in the field, based on spectral image data within each of the crop evaluation zones in the image.

2. The computing system of claim 1 wherein the spatial filtering logic identities the crop evaluation zone for each crop row in the field, defining a geographic margin window around the geographic location of where a corresponding crop row was planted in the field.

3. The computing, system of claim 2 and further comprising:

spectral filtering logic that filters spectral information in each of the crop evaluation zones to identify a crop density in each of the crop evaluation zones.

4. The computing system of claim 3 wherein the spectral filtering logic confines the filtering of the spectral information to the spectral information in each of the crop evaluation zones.

5. The computing system of claim 3 and further comprising:
    grid generation logic that divides the image of the field into a grid with grid sections, each grid section corresponding to a geographic area in the field.

6. The computing system of claim 5 wherein the emergence metric generation logic generates an emergence metric, indicative of an emergence characteristic, corresponding to each grid section in the grid.

7. The computing system of claim 6 and further comprising:
    a runtime system that detects a user request input and generates a crop display that visually displays the grid sections and visual indicia indicative of the corresponding emergence metrics.

8. The computing system of claim 7 wherein the runtime system displays color coded grid sections as the visual indicia corresponding to the emergence metric for each grid section.

9. The computing system of claim 7 wherein the runtime system displays alphanumeric information on each of the grid sections as the visual indicia corresponding to the emergence metric for each grid section.

10. The computing system of claim 8 and further comprising:
    video link generation logic that generates a user actuatable link, for each given grid section, the user actuatable link linking to a video image of the field, corresponding to the given grid section.

11. A method, comprising:
    receiving a field image of a field;
    receiving pre-determined crop row location data generated when crop was planted in the field and being indicative of a geographic location where rows of crops were planted in the field;
    identifying a set of crop evaluation zones, each encompassing a row in the field, on the image, based on the crop location data;
    performing spectral filtering on the crop evaluation zone to identify crops based on spectral image data in the crop evaluation zones;
    identifying a plurality of different grid sections, each corresponding to a different geographic location in the field;
    generating an emergence metric indicative of an emergence characteristic of the identified crops in each of the grid sections based on an emergency metric value in portions of the crop evaluation zones included in each grid section; and
    generating a user interface indicative of the emergence metric visually corresponding to each of the grid sections.

12. The method of claim 11 wherein generating an emergence metric comprises:
    filtering spectral information in each crop evaluation zones to identify a crop density in each crop evaluation zone.

13. The method of claim 12 and further comprising:
    detecting a user request input; and generating a crop display that visually displays the grid sections and visual indicia indicative of the corresponding emergence metrics.

14. The method of claim 13 wherein generating a crop display comprises:

generating color coded grid sections as the visual indicia corresponding to the emergence metric for each grid section.

15. The method of claim 13 wherein generating a crop display comprises:

generating alphanumeric information on each of the grid sections as the visual indicia corresponding to the emergence metric for each grid section.

16. The method of claim 13 wherein generating a crop display comprises:

generating a user actuatable link, for each given grid section, the user actuatable link being actuated to navigate to a video image of the field, corresponding to the given grid section.

17. A computing system, comprising:

spatial filtering logic that receives image data indicative of an image of a field and pre-determined, crop location data generated when crop was planted in the field and being indicative of a geographic location of where crop rows were planted in the field, and that identifies a crop evaluation zone for each crop row in the field, each crop evaluation zone defining a geographic window around the geographic location of where a corresponding crop row was planted in the field;

spectral filtering logic that filters spectral information in the crop evaluation zones to identify a crop density in each of the crop evaluation zones;

grid generation logic that divides the image of the field into a grid with grid sections, each grid section corresponding to a geographic area in the field;

emergence metric generation logic that logic generates an emergence metric, indicative of an emergence characteristic value, for each geographic area in the field corresponding to each grid section in the grid; and a user interface component that generates a crop display that visually displays the grid sections and visual indicia indicative of the corresponding emergence metrics.

18. The computing system of claim 17 and further comprising:

video link generation logic that generates a user actuatable link, for each given grid section, the user interface component displaying the user actuatable link for each given grid section on the given grid section on the crop display, each link being actuatable to navigate to a video image of a portion of the field, corresponding to the given grid section.

* * * * *